United States Patent
Wang et al.

(10) Patent No.: US 9,801,981 B2
(45) Date of Patent: Oct. 31, 2017

(54) MEDICAL DEVICE BALLOONS WITH IMPROVED STRENGTH PROPERTIES AND PROCESSES FOR PRODUCING THE SAME

(75) Inventors: Lixiao Wang, Long Lake, MN (US); John Jianhua Chen, Plymouth, MN (US); Jeffrey S. Lindquist, Maple Grove, MN (US); Nao Pao Lee, Brooklyn Park, MN (US); Douglas A. Devens, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1098 days.

(21) Appl. No.: 13/593,756

(22) Filed: Aug. 24, 2012

(65) Prior Publication Data
US 2012/0323301 A1    Dec. 20, 2012

Related U.S. Application Data

(62) Division of application No. 11/356,522, filed on Feb. 17, 2006, now abandoned, which is a division of application No. 10/087,653, filed on Feb. 28, 2002, now Pat. No. 7,029,732.

(51) Int. Cl.
| | |
|---|---|
| *A61M 29/00* | (2006.01) |
| *A61L 31/06* | (2006.01) |
| *A61M 25/10* | (2013.01) |
| *B29C 47/00* | (2006.01) |
| *B29C 47/86* | (2006.01) |
| *A61L 31/12* | (2006.01) |
| *B29C 47/82* | (2006.01) |
| *B29C 47/88* | (2006.01) |
| *B29L 31/00* | (2006.01) |

(52) U.S. Cl.
CPC ............ *A61L 31/06* (2013.01); *A61L 31/125* (2013.01); *A61M 25/1029* (2013.01); *B29C 47/0004* (2013.01); *B29C 47/0023* (2013.01); *B29C 47/822* (2013.01); *B29C 47/86* (2013.01); *B29C 47/862* (2013.01); *B29C 47/8895* (2013.01); *B29L 2031/7542* (2013.01); *Y10T 428/1086* (2015.01)

(58) Field of Classification Search
USPC .................. 604/96.01–103.14; 606/191–192; 623/1.11–1.35
See application file for complete search history.

(56) References Cited

U.S. PATENT DOCUMENTS

| | | | |
|---|---|---|---|
| 3,508,554 A | 4/1970 | Sheridan | |
| 3,946,100 A | 3/1976 | Davis et al. | |
| 4,296,058 A | 10/1981 | Chen et al. | |
| 4,490,421 A | 12/1984 | Levy | |
| 4,867,881 A | 9/1989 | Kinzer | |
| 4,906,244 A | 3/1990 | Pinchuk et al. | |
| 4,935,190 A | 6/1990 | Tennerstedt | |
| 4,950,239 A | 8/1990 | Gahara et al. | |
| 4,963,313 A | 10/1990 | Noddin et al. | |
| 4,988,279 A | 1/1991 | Belcher | |
| 5,007,898 A * | 4/1991 | Rosenbluth et al. | ......... 606/108 |
| 5,030,227 A * | 7/1991 | Rosenbluth et al. | ......... 606/192 |
| 5,152,781 A | 10/1992 | Tang et al. | |
| 5,250,069 A | 10/1993 | Nobuyoshi et al. | |
| 5,264,260 A * | 11/1993 | Saab | ............................ 428/35.5 |
| 5,270,086 A | 12/1993 | Hamlin | |
| 5,306,246 A | 4/1994 | Sahatjian et al. | |
| 5,312,430 A * | 5/1994 | Rosenbluth et al. | ......... 606/192 |
| 5,328,468 A | 7/1994 | Kaneko et al. | |
| 5,344,400 A | 9/1994 | Kaneko et al. | |
| 5,358,486 A * | 10/1994 | Saab | ........................ 604/103.13 |
| 5,403,304 A | 4/1995 | Ishida | |
| 5,411,477 A | 5/1995 | Saab | |
| 5,500,180 A * | 3/1996 | Anderson et al. | ............. 264/532 |
| 5,527,336 A * | 6/1996 | Rosenbluth et al. | ......... 606/192 |
| 5,556,383 A * | 9/1996 | Wang et al. | ............. 604/103.11 |
| 5,662,960 A | 9/1997 | Hostettler et al. | |
| 5,714,110 A | 2/1998 | Wang et al. | |
| 5,752,971 A * | 5/1998 | Rosenbluth et al. | ......... 606/192 |
| 5,755,690 A * | 5/1998 | Saab | ........................ 604/103.06 |
| 5,797,877 A | 8/1998 | Hamilton et al. | |
| 5,830,182 A * | 11/1998 | Wang et al. | ............... 604/96.01 |
| 5,833,657 A * | 11/1998 | Reinhardt et al. | ....... 604/101.02 |

(Continued)

FOREIGN PATENT DOCUMENTS

| | | |
|---|---|---|
| EP | 0540858 | 9/1992 |
| EP | 0768097 | 4/1997 |

(Continued)

OTHER PUBLICATIONS

ASTM D-638, "Standard Test Method for Tensile Properties of Plastics", ASTM International, 2012, pp. 1-13.
ASTM D-882, "Standard Test Method for Tensile Properties of Thin Plastic Sheeting", ASTM International, 2012, pp. 1-9.
Bashford, David, "Thermoplastics: Directory and Databook", Padstow, Bornwall, GB: Chapman & Hall, 1997, Ed. First, pp. 339-352.
Bundara, B. "Influence of Moisture on Impact Fracture Behaviour of Polymers as Exemplified by Polyamide 66", London: Mechanical Engineering Publications, 1995, pp. 305-314.
Data Sheet for PEBAX 7033 SA 01, Technical Polymers, 2008, p. 1.
Handbook of Thermoplastic Polyesters, Homopolymers, Copolymers, Blends and Composites, Edited by AIP Press, Copyright 1996, Edited by James Mark, ISBN 1-56396-295-0.

(Continued)

*Primary Examiner* — Amy R Weisberg
(74) *Attorney, Agent, or Firm* — Seager, Tufte & Wickhem LLP.

(57) ABSTRACT

A tubular parison for forming a medical device balloon. The parison is formed of a polymeric material, for instance a thermoplastic elastomer. The parison has an elongation at break which is not more than 80% of the elongation of the bulk polymeric material. The elongation of the parison is controlled by altering extrusion conditions. Balloons prepared from the parisons provide higher wall strength and/or higher inflation durability than balloons prepared from conventional parisons of the same material.

9 Claims, No Drawings

(56) References Cited

U.S. PATENT DOCUMENTS

| | | | |
|---|---|---|---|
| 5,836,951 A * | 11/1998 | Rosenbluth et al. | 606/108 |
| 5,849,846 A | 12/1998 | Chen et al. | |
| 5,932,307 A | 8/1999 | Ryan et al. | |
| 5,951,941 A * | 9/1999 | Wang et al. | 264/523 |
| 6,017,577 A | 1/2000 | Hostettler et al. | |
| 6,024,722 A | 2/2000 | Rau et al. | |
| 6,146,356 A * | 11/2000 | Wang et al. | 604/96.01 |
| 6,176,698 B1 | 1/2001 | Grantz et al. | |
| 6,210,364 B1 * | 4/2001 | Anderson et al. | 604/96.01 |
| 6,268,026 B1 | 7/2001 | Jester et al. | |
| 6,270,522 B1 | 8/2001 | Simhambhatla et al. | |
| 6,325,780 B1 | 12/2001 | Schaible et al. | |
| 6,383,212 B2 * | 5/2002 | Durcan et al. | 623/1.11 |
| 6,406,457 B1 * | 6/2002 | Wang et al. | 604/96.01 |
| 6,416,494 B1 | 7/2002 | Wilkins | |
| 6,416,832 B1 | 7/2002 | Uehara et al. | |
| 6,527,741 B1 | 3/2003 | Lee et al. | |
| 6,596,219 B2 | 7/2003 | Dutta et al. | |
| 6,620,127 B2 | 9/2003 | Lee et al. | |
| 6,796,958 B2 | 9/2004 | Chen et al. | |
| 6,863,861 B1 | 3/2005 | Lee et al. | |
| 6,875,197 B1 | 4/2005 | Simhambhatla et al. | |
| 6,955,658 B2 | 10/2005 | Murray, III | |
| 6,986,785 B2 | 1/2006 | O'Shaughnessy et al. | |
| 7,029,732 B2 | 4/2006 | Wang et al. | |
| 7,947,059 B2 | 5/2011 | Chin et al. | |
| 2001/0003796 A1 | 6/2001 | Yang et al. | |
| 2001/0006700 A1 | 7/2001 | Nazarova et al. | |
| 2003/0167067 A1 | 9/2003 | Wang et al. | |
| 2004/0191443 A1 | 9/2004 | Hamlin | |
| 2004/0207127 A1 | 10/2004 | Hamlin | |
| 2005/0146085 A1 | 7/2005 | Holman et al. | |
| 2005/0233025 A1 | 10/2005 | Zhang et al. | |
| 2006/0033241 A1 | 2/2006 | Schewe et al. | |
| 2006/0151921 A1 | 7/2006 | Wang et al. | |

FOREIGN PATENT DOCUMENTS

| | | |
|---|---|---|
| GB | 2059328 | 4/1981 |
| GB | 2342310 | 4/2000 |
| JP | 2002331034 | 11/2002 |
| WO | 9803218 | 1/1998 |
| WO | 9836783 | 8/1998 |
| WO | 9964101 | 12/1999 |
| WO | 0226308 | 4/2002 |

OTHER PUBLICATIONS

Rudin, Alfred, "The Elements of Polymer Science and Engineering", New York: Academic Press, 1982, pp. 422-423.
S. Levy, "Improved Dilational Catheter Ballons", J. Clinical Engineering, vol. 11, No. 4, Jul.-Aug. 1986, 291-295, at p. 293.
Walker, Benjamin F., "Handbook of Thermoplastic Elastomers", New York: Van Nostrand Reinhold Company, 1982, pp. 62, 63 & 186 to 189.

* cited by examiner

MEDICAL DEVICE BALLOONS WITH IMPROVED STRENGTH PROPERTIES AND PROCESSES FOR PRODUCING THE SAME

CROSS-REFERENCE TO RELATED APPLICATIONS

This application is a divisional of U.S. patent application Ser. No. 11/356,522, filed Feb. 17, 2006, abandoned on Feb. 17, 2006, which is a divisional of U.S. application Ser. No. 10/087,653, filed Feb. 28, 2002, issued as U.S. Pat. No. 7,029,732, on Apr. 18, 2006, the contents of which are hereby incorporated herein by reference.

BACKGROUND OF THE INVENTION

Medical devices comprising catheter balloons are used in an increasingly widening variety of applications including vascular dilatation, stent delivery, drug delivery, delivery and operation of sensors and surgical devices such as blades, and the like. The desired physical property profile for the balloons used in these devices vary according to the specific application, but for many applications a high strength robust balloon is necessary and good softness and trackability properties are highly desirable.

Commercial high strength balloons having wall strengths in excess of 20,000 psi, have been formed of a wide variety of polymeric materials, including PET, nylons, polyurethanes and various block copolymer thermoplastic elastomers. U.S. Pat. No. 4,490,421, Levy and U.S. Pat. No. 5,264,260, Saab describe PET balloons. U.S. Pat. No. 4,906,244, Pinchuk et al, and U.S. Pat. No. 5,328,468, Kaneko, describe polyamide balloons. U.S. Pat. No. 4,950,239, Gahara, and U.S. Pat. No. 5,500,180, Anderson et al describe balloons made from polyurethane block copolymers. U.S. Pat. No. 5,556,383, Wang et al and U.S. Pat. No. 6,146,356, Wang et al, describes balloons made from polyether-block-amide copolymers and polyester-block-ether copolymers. U.S. Pat. No. 6,270,522 Simhambhatla, et al, describes balloons made from polyester-block-ether copolymers of high flexural modulus. U.S. Pat. No. 5,344,400, Kaneko, describes balloons made from polyarylene sulfide. All of these balloons are produced from extruded tubing of the polymeric material by a blow-forming radial expansion process. U.S. Pat. No. 5,250,069, Nobuyoshi et al, U.S. Pat. No. 5,797,877, Hamilton et al, and U.S. Pat. No. 5,270,086, Hamlin, describe still further materials which may be used to make such balloons.

Different balloon materials provide different properties. In general, materials with high elongation and low flexural modulus give relatively greater resistance to pin hole formation and to winging upon deflation and also provide better trackability through body lumens, but such materials tend to give balloons with lower burst strengths and higher distensibility. Conversely, polymer materials with relatively high tensile strengths and hardness tend to give balloons with low distension and high burst strengths, but at a sacrifice of susceptibility to pin holing, winging and/or loss of trackability.

A variety of blow forming techniques have been utilized. The extruded parison may be radially expanded as is into a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison. Examples of these techniques may be found in the patent documents already mentioned or in U.S. Pat. No. 4,963,313, Noddin et al, U.S. Pat. No. 5,306,246 Sahatjian, U.S. Pat. No. 4,935,190, Tennerstedt, U.S. Pat. No. 5,714,110, Wang et al.

Following blow-forming the balloons may be simply cooled, heat set at a still higher pressure and/or temperature or heat shrunk at an intermediate pressure and/or temperature, relative to the blow forming temperature and pressure. See U.S. Pat. No. 5,403,340, Wang et al, EP 54,0858 Advanced Cardiovascular Systems, Inc., WO 98/03218, Scimed Life Systems.

Thus a great deal of attention has been paid to blow forming processing conditions and to balloon materials. Less attention has been paid to extrusion conditions for preparing the polymer tubing used as the parison. In general, dry polymer has been used. It has been recognized that a single die can be used to produce different tubing diameters by varying the draw down ratio, but, at least since the advent of PET balloons, relatively low draw down ratios have been recommended to provide an amorphous state and thereby facilitate the subsequent blow-forming step. See S. Levy, "Improved Dilatation Catheter Balloons," *J. Clinical Engineering*, Vol. 11, No. 4, July-August 1986, 291-295, at p 293.

Balloons made from thermoplastic elastomers are desirable because they are relatively soft and robust, have good trackability and still provide adequate strength for many applications. However, as demands for balloon performance have increased, a need has arisen to find a way to improve wall strength of thermoplastic elastomer balloons without requiring still further increases in hoop ratios, and/or to provide more robust balloons without sacrificing wall strength.

SUMMARY OF THE INVENTION

The present invention is directed to methods of forming balloons and parisons therefor.

Surprisingly, it has been found that improved balloon properties can be obtained by controlling the parison extrusion in a manner which restricts the elongation of the parison material in the longitudinal direction. In one aspect the invention is a method of extruding a parison useful for forming a medical balloon by a radial expansion process, the method comprising extruding the parison in a manner which provides the parison material with an elongation which is not more than 80% of the elongation of the bulk material. In another aspect the invention is a method of extruding a parison, the method comprising extruding a tube of polymeric material to form the tube at a cross-sectional area draw down ratio of about 8 or higher.

In still another aspect, the invention is directed to improved balloons characterized by a particular high strength property; to medical devices comprising such balloons; and to surgical procedures employing such devices. A particular embodiment is a balloon formed from a thermoplastic elastomer and having a wall strength of at least 34,000 psi, especially at least 37,000 psi, in pre-sterilized condition. A further embodiment is such a balloon, in post-sterilized condition, having a wall strength of 32,000 psi or more.

Further aspects of the invention are described in the following detailed description of the invention or in the claims.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

It has been found that the distention and the burst pressure of a balloon are affected by the elongation properties of the extruded parison, as well as by the hoop ratio and the tube wall thickness. It is believed the elongation affects the balloon properties through its effect on the balloon wall thickness. Thus, for a given hoop ratio and tube size, as parison elongation decreases, the balloon wall thickness increases, the balloon distention decreases and the burst pressure increases.

Thus, while an increase in the hoop strength and modulus comes at the expense of thinner balloon walls, which can increase distention and decrease burst pressure, it is also possible to extrude tubes with lower elongation to break. This allows one to provide even stronger walls than were previously been obtained with a given polymer. Alternatively, the invention can allow one to thicken the balloon wall, while affecting the hoop strength and distention very little, thereby obtaining a balloon which is more suited to stent or other surgical device delivery operations.

In one aspect the invention involves modifying the parison processing so as to provide the parison material with an elongation which is not more than 80% of the elongation of the bulk material. In particular, when 3 inch length of the extruded tube is stretched until it breaks, the length of the tube when it breaks will correspond to a percentage increase which is not more than 80% of the elongation value obtained by determining elongation of the bulk material per ASTM D-638. In some embodiments the parison is processed so as to provide the parison material with an elongation which is not more than 70% of the elongation of the bulk material, and in still others the parison elongation is less than 60% of the elongation of the bulk material.

The parison processing techniques described herein, alone or in combination can provide balloon wall strength improvements of as much as 10-25% over those obtainable in their absence, for non-sterilized balloons. Sterilization, depending on the technique chosen, may reduce this benefit somewhat. The invention may be used with any known balloon materials, however high strength thermoplastic elastomers are preferred, especially polyamide/polyether block copolymers, including polyamide/polyether/polyesters such as sold under the PEBAX trademark, in particular PEBAX 7033 and PEBAX 7233; polyester/polyether block copolymers such as sold under the HYTREL and ARNITEL trademarks, in particular ARNITEL EM 740 and HYTREL 8238; and polyurethane block copolymers such as PELLETHANE 2363-75D.

The parison may be extruded as a single layer or in multiple layers, for instance 3, 5, 7, or even more alternating layers of PEBAX 7033 and Pebax 7233. Blends of such polymers may also be used.

Parison elongation may be controlled by varying one or more of the following extrusion parameters:

Extrusion Temperature:

The temperature at the extrusion head, die temperature, is lowered relative to the temperature in the extruder barrel. Heat loss begins even as the material is passing through the die head. The resulting tubing has a higher degree of crystallization. In general the die head temperature reduction should be about 5 to about 50° F., suitably 10° F. to 40° F., and preferably about 20-30° F. below the barrel temp.

Draw Down Ratio:

Die configuration, extruder pressure and/or line speeds can be adjusted to provide a cross-sectional area draw down ratio in excess of 5:1. Ratios as high as 17:1 have been employed, and even higher ratios may be advantageous because they reduce extruder pressure demands. Typically the draw down ratios will be in the range of about 8:1 to about 17:1.

Quench Time:

Decreasing the gap between the extrusion head and the cooling bath tank can also lower parison elongation by shortening the quench time. Quench time can also be shortened by increasing the line speed.

Bath Temperature:

Maintaining the cooling bath at a lower temperature also can lower the elongation of the parison.

A surprising benefit of at least some embodiments of the invention is that balloons prepared from parisons of the invention have improved resistance to repeat inflation bursts versus controls utilizing the same polymer, but prepared using typical extrusion parameters for commercial balloons.

The improvement may permit three times, or even more, the number of inflations to rated pressure, compared to the controls.

The invention is illustrated by the following non-limiting examples.

EXAMPLES

In the following examples the following abbreviations are used.

| | |
|---|---|
| Ex | Example No. Alphabetic series are comparative, numeric series are invention examples. |
| ID | Internal diameter, as extruded. |
| OD | Outer diameter, as extruded. |
| Die temp | Extruder die zone temperature in degrees Fahrenheit. The extruder barrel was kept at 395° F. in these examples. |
| Line speed | Speed in feet/min of the puller. |
| DDR | Draw down ratio of the cross-sectional area from extrusion head opening, to final tube dimensions. DDR = [(Die ID)$^2$ − (Tip OD)$^2$]/ [(Tubing OD)$^2$ − (Tubing ID)$^2$] |
| Elong @ break | Given as percentage elongation determined on a 3" long extruded tube which is stretched to break. |
| Balloon 2x wall | Thickness in inches of the balloon double wall as measured with a micrometer. |
| Hoop | Hoop ratio determined as balloon OD (mold diameter)/parison ID (as extruded). |
| Distension | The change in diameter as a % of start diameter for the stated ranges of 6:12 (6 atm to 12 atm) and 12:18 (12 atm to 18 atm) inflation pressure. |
| Burst | Pressure in psi at which the balloon burst |
| Burst strength | Wall strength at burst as calculated by the equation: $T_s = PD/2t$ where: $T_s$ is the wall tensile strength; P is the balloon burst pressure; D is the nominal diameter of the balloon; and t is the wall thickness. |

All values are averages of at least 6 balloons. Balloon blowing conditions used the same times, temperatures and sequences, except where indicated.

All data is for balloons having a nominal diameter of 3.0 mm at 6 atm. The balloons were made from PEBAX 7033. The published elongation value for the bulk polymer, per ASTM D-638, is 400%. The balloons were made from conventionally extruded parisons using a very high hoop ratio and a step-wise dipping process similar to that described in Wang et al, Example 3, U.S. Pat. No. 5,714,110. A typical program is as follows:

| Program: | bath at | 95° C. |
|---|---|---|
| (1) | pressure to | 100 psi |
| | tension to | 50 g |
| | dip to D | 8 seconds |
| | hold at D | 6 seconds |
| (2) | pressure to | 450 psi |
| | tension to | 20 g |
| | dip to C | 4 sec |
| | hold at C | 6 seconds |
| (3) | pressure to | 550 psi |
| | tension to | 200 g |
| | dip to B | 20 sec |
| | hold at B | 6 seconds | where D, C and B are locations, as described in U.S. Pat. No. 5,714,110. The parison formation conditions and formed balloon results are described in Table 1. Die configuration was not varied between examples. Tank gaps, die temperatures and speeds were varied as needed to obtain parison elongation targets. Extruder pressure was not independently controlled and varied as a result of changing these conditions.

Table 1 provides an example of a balloon formed using conventional tube processing at a high hoop ratio.

TABLE 1

| | | | | | | | | | | | | |
|---|---|---|---|---|---|---|---|---|---|---|---|---|
| | | | | | | Control | | | | | | |
| Ex | Tube ID | Tube OD | Die Temp | Line Speed | DDR | Elong @ break | Balloon 2X wall | Hoop | Distension 6:12 | Distension 12:18 | Burst | Burst Strength |
| A | .0177 | .0321 | 395 | 24 | 3.5 | 367 | .00116 | 6.9 | 5.6 | 4.4 | 301 | 31056 |

The elongation at break of this parison corresponds to about 91% of the published value for the bulk polymer.

Table 2 gives the results of the same balloon wall thickness made in accordance with the invention by increasing the DDR. The increased draw down ratio reduced the elongation of this tube to about 48% of the published elongation value.

TABLE 2

| | | | | | | | | | | | | |
|---|---|---|---|---|---|---|---|---|---|---|---|---|
| | | | | | | High Draw Down | | | | | | |
| Ex | Tube ID | Tube OD | Die Temp | Line Speed | DDR | Elong @ break | Balloon 2X wall | Hoop | Distension 6:12 | Distension 12:18 | Burst | Burst Strength |
| 1 | .0176 | .0310 | 395 | 50 | 12.1 | 190 | 0.00118 | 6.9 | 5.4 | 4.5 | 331 | 34411 |

Table 3 shows extrusion parameters and balloon property results when, after extrusion, the parison was modified by one of the following steps before it was blow-formed into a balloon.

Example 2

A freeze spray process was used to selectively reduce parison cone and waists as per Example 1 of U.S. Pat. No. 5,807,520.

Example 3

Cones and waists were selectively reduced by a grinding and necking process which did not stretch the body-forming portion of the parison. Similar to Example 2, first paragraph of PCT/U.S. Pat. No. 01/26140, filed Aug. 22, 2001, corresponding to U.S. application Ser. No. 09/672330 filed Sep. 28, 2000.

Example 4 the entire parison was stretched longitudinally at ambient temperature under internal pressurization to maintain ID at the extruded dimension (±4%) at a stretch ratio 3×, where × is starting length. See control in Example 1 of PCT/U.S. Pat. No. 01/26140.

TABLE 3

Parison Modifications

| Ex | Tube ID | Tube OD | Die Temp | Line Speed | DDR | Elong @ break | Balloon 2X wall | Hoop | Distension 6:12 | Distension 12:18 | Burst | Burst Strength |
|---|---|---|---|---|---|---|---|---|---|---|---|---|
| 2 | 0.176 | .0290 | 395 | 50 | 12:1 | 193 | .00105 | 6.9 | 5.3 | 4.7 | 309 | 36101 |
| 3 | .0176 | .0290 | 395 | 50 | 12:1 | 193 | .00098 | 6.9 | 4.8 | 4.8 | 297 | 37423 |
| 4 | .0176 | .0290 | 395 | 50 | 12:1 | 193 | .00097 | 6.9 | 4.9 | 4.7 | 300 | 37577 |

In examples 2-4, the burst pressure in all cases was comparable to the control balloon, but with thinner walls so the wall strength is much improved over the control balloon.

Example 5

Balloons were made using PEBAX 7033 parisons stretched at ambient temperature at a stretch ratio of 1.5× and a hoop ratio of 7.0. Parisons, extruded to keep the parison elongation at break above 80% of the published elongation of the polymer, were used as controls. Parisons, extruded to provide a parison elongation at break of about 50% or less of the published elongation of the polymer, were prepared as invention examples. The balloons were inflated to 211 psi and deflated repeatedly. Four balloons were present in each group. The control balloon group, on average, failed at about 80 repeats. All of the balloons of the invention group survived 235 repeats without failure, at which point the test was discontinued.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A medical device balloon formed of a thermoplastic elastomer polymeric material and having a tensile wall strength in excess of 34,000 psi in pre-sterilized condition.

2. A medical device balloon as in claim 1 wherein said tensile wall strength in excess of 37,000 psi in pre-sterilized condition.

3. A medical device balloon as in claim 1 wherein the polymeric material comprises a polyamide/polyether/polyester, a polyester/polyether block copolymer, a polyurethane block copolymer or a mixture thereof.

4. A medical device balloon as in claim 1 wherein the polymeric material is a polyamide/polyether/polyester.

5. A medical device balloon as in claim 1 formed with a single layer of said polymeric material.

6. A medical device balloon as in claim 1 comprising of a plurality of layers of said polymeric material.

7. A medical device comprising a balloon as in claim 1 mounted on a catheter.

8. A medical device as in claim 7 further comprising a stent mounted on the catheter.

9. A medical device balloon formed of a thermoplastic elastomer polymeric material and having a tensile wall strength, in post-sterilized condition, of 32,000 psi or more.

\* \* \* \* \*